(12) United States Patent
Orrico

(10) Patent No.: US 6,170,485 B1
(45) Date of Patent: Jan. 9, 2001

(54) ANTI-SNORING DEVICE

(76) Inventor: Anthony J. Orrico, 112 Quayside Dr., Jupiter, FL (US) 33477

(*) Notice: Under 35 U.S.C. 154(b), the term of this patent shall be extended for 0 days.

(21) Appl. No.: 09/437,834

(22) Filed: Nov. 10, 1999

(51) Int. Cl.[7] .................................................. A61F 5/56
(52) U.S. Cl. ...................... 128/848; 602/902; 128/859; 128/862
(58) Field of Search .................. 128/848, 859–862; 433/6, 7; 602/902

(56) References Cited

U.S. PATENT DOCUMENTS

| | | | |
|---|---|---|---|
| 2,833,278 | * 5/1958 | Ross | 128/862 |
| 4,169,473 | 10/1979 | Samelson . | |
| 5,082,007 | * 1/1992 | Adell | 128/859 |
| 5,117,816 | 6/1992 | Shapiro et al. . | |
| 5,365,945 | * 11/1994 | Halstrom | 128/848 |
| 5,499,633 | * 3/1996 | Fenton | 128/848 |
| 5,566,683 | 10/1996 | Thornton . | |
| 5,794,627 | 8/1998 | Frantz et al. . | |
| 5,810,013 | 9/1998 | Belfer . | |
| 5,823,193 | 10/1998 | Singer et al. . | |
| 5,884,628 | 3/1999 | Hilsen . | |

* cited by examiner

Primary Examiner—Michael A. Brown
(74) Attorney, Agent, or Firm—George Pappas

(57) ABSTRACT

An anti-snoring device including detachably attachable upper and lower trays selectively fitting over a person's upper and lower teeth. The trays are formed of a rigid plastic outer shell and include an inner thermoplastic moldable portion. Tongues are integrally formed with the rigid outer shells and extend from each of the upper and lower trays forwardly from the central portions of the upper and lower trays. The tongues are selectively detachably attachable to one another in a plurality of positions and for shifting the lower tray and jaw slightly forward from its normal position. Depressions are formed in the lower and upper trays which align and form breathing openings between the upper and lower trays on each side of the trays central portions. The trays posterior portions terminate prior to the person's molars or at about the person's premolars.

29 Claims, 2 Drawing Sheets

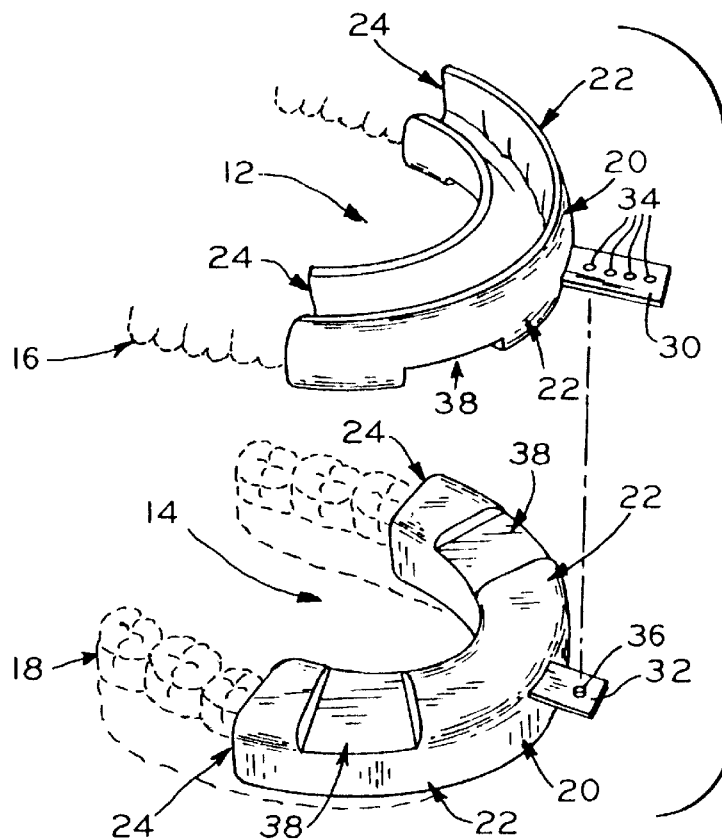
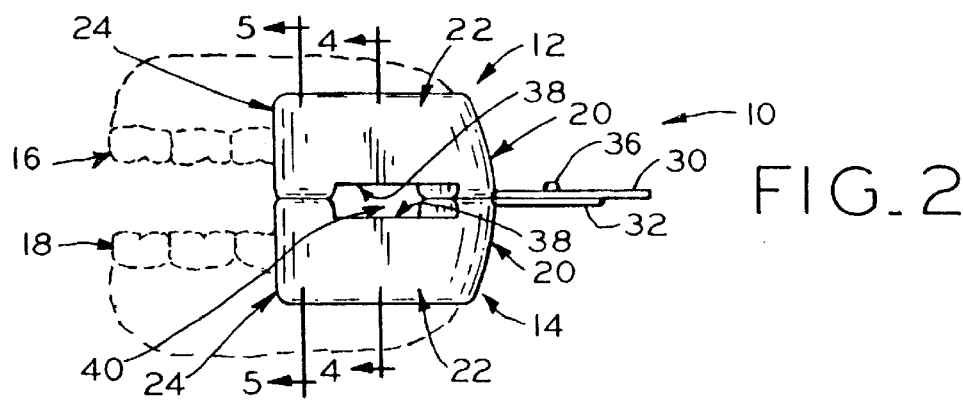
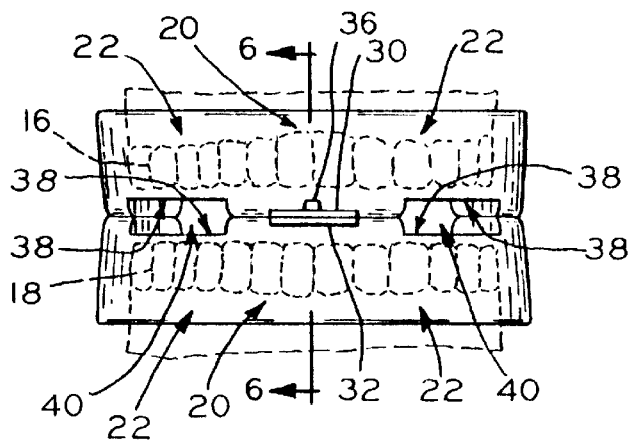

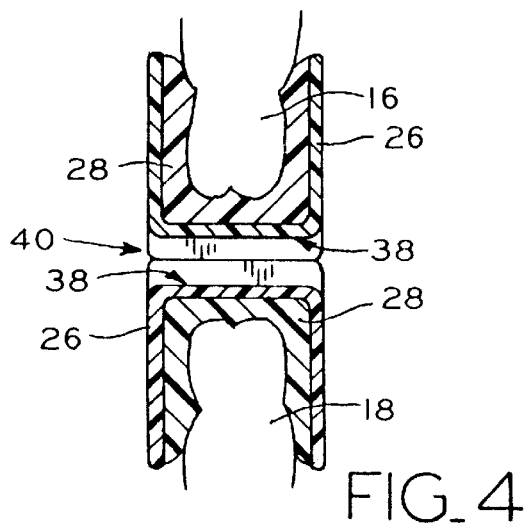
FIG_4
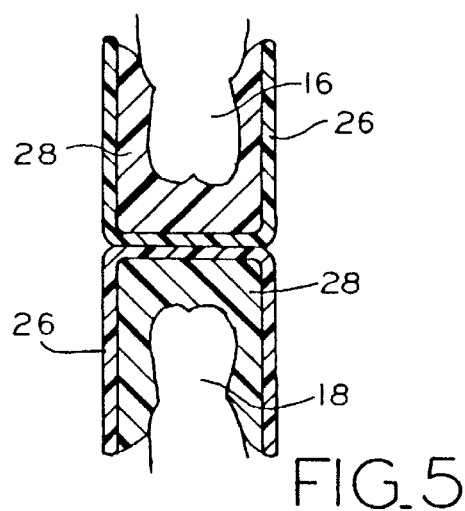
FIG_5
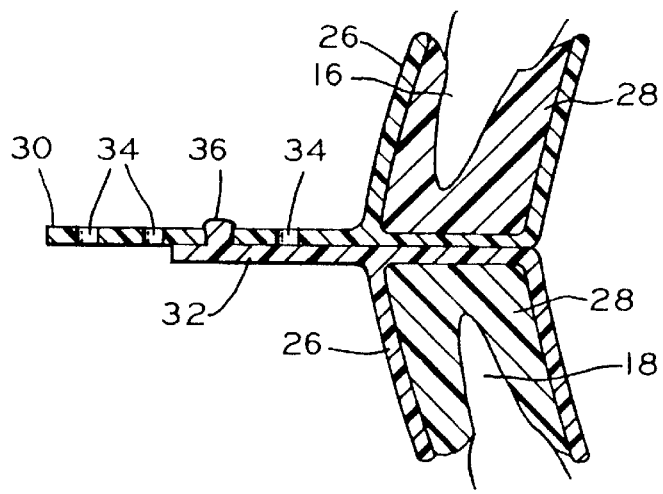
FIG_6
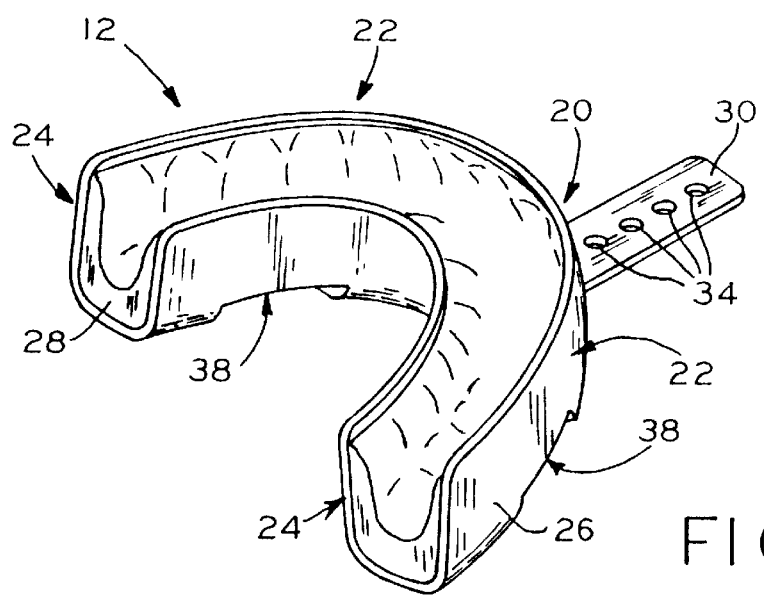
FIG_7

ANTI-SNORING DEVICE

TECHNICAL FIELD

The present invention relates to the technical field of dental devices used for alleviating snoring. More particularly, the present invention relates to a dental device that prevents snoring by forcing the person's lower jaw to protrude slightly forward from its normal position.

BACKGROUND OF THE INVENTION

Snoring is problematic for many people and affects both the snorer as well as the individuals around him. Snoring is problematic not only in view of the noise, but also because it essentially interferes with the normal breathing of the snorer. It is known that snoring is caused by the tongue relaxing and, thus contributing to the blocking of the air passageway in the pharynx or lingual compartment. As the tongue relaxes, it falls backwardly blocking the breathing airway and thus, as air forcibly passes through the airway, loud vibrations are created generally between the tongue and other tissues in the air passageway.

It is known that snoring can be alleviated by pulling or otherwise forcing the individual's lower jaw forward of its normal position. This essentially pulls the tongue forwardly and away from the air passageway thereby effectively preventing blockage of the air passageway and also preventing snoring. Many different anti-snoring devices have been suggested for essentially pulling the individual's lower jaw slightly forwardly while sleeping. Several such examples are shown and disclosed in the following US patents: Samelson, U.S. Pat. No. 4,169,473; Thornton, U.S. Pat. No. 5,566,683; Frantz et al., U.S. Pat. No. 5,794,627; Shapiro et al., U.S. Pat. No. 5,117,816; Belfer, U.S. Pat. No. 5,810,013, Singer et al., U.S. Pat. No. 5,823,193 and Hilsen, U.S. Pat. No. 5,884,628.

Although these anti-snoring devices would appear to function properly and alleviate snoring, they are not without shortcomings and drawbacks. These prior anti-snoring devices, in general, appear to be difficult to fit over a person's teeth or may required a skilled dentist for fitting, can be generally expensive to manufacture and apply, and may also generally be difficult to actually use while sleeping. Accordingly, a need exists for an improved anti-snoring device that can be manufactured and sold fairly inexpensively, typically without the need for a dentist for fitting and, further, which is fairly easily usable by the snorer and which is effective in preventing snoring and enhancing unrestricted breathing.

SUMMARY OF THE INVENTION

It is the principal object of the present invention to overcome the above-discussed disadvantages associated with prior anti-snoring devices.

The present invention overcomes the disadvantages associated with prior anti-snoring devices by providing upper and lower trays having a generally rigid outer shell and an inner moldable portion adapted to fit over a person's upper and lower teeth. The outer rigid shells are generally U-shaped and are arcuate extending from a central portion adapted to fit over a person's front teeth to posterior portions on each side of the central portion. The outer rigid shells are injection molded and made of generally rigid plastic material, whereas the inner moldable portions are made of a thermoplastic material capable of being molded at temperatures greater than about 115° F. Thus, for fitting the upper and lower trays over a person's teeth, the trays are heated such as by placing in hot water greater than 115° F. and, thereafter, are placed over a person's teeth causing the inner thermoplastic moldable portions to be shaped or fitted over the person's upper and lower teeth.

To enhance and allow breathing through the person's mouth, the rigid outer shells include depressions in the posterior portions on each side of the central portion such that, when the trays are placed on a person's upper and lower teeth, the upper tray depressions are aligned with the lower tray depressions thereby providing breathing openings on each side of the central portion and between the trays. When placed on a person's teeth, although the upper and lower trays are adjacent and in contact with one another at the central portion and terminal ends of the posterior portions, breathing openings are provided between the trays on either side of the central portions wherethrough the person may easily breath through the mouth. Additionally, the posterior portions of both the upper and lower trays are sized so as to extend a distance on each side of the central portions and terminate at about the person's premolars and prior to the molars. In this manner, gagging is effectively prevented thereby making the anti-snoring device more practical and usable while yet further enhancing breathing through the person's mouth.

So as to selectively locate the lower jaw slightly forwardly from its normal position, the upper and lower trays are provided with tongues which are integrally formed with the upper and lower rigid shells and extend forwardly from the central portions. When the trays are placed on a person's teeth, the tongues are located adjacent and parallel with one another. One of the tongues is provided with a plurality of aligned holes, whereas the other tongue includes a projection adapted to selectively snap fit into any one of the other tongue holes. The holes extend generally in a line forwardly of the central portions. Thus, the upper and lower trays are detachably attachable to one another by snap fitting the projection in to any one of the plurality of holes. The lower tray can thus be detachably attached to the upper tray in a plurality of positions as may be desirable or tolerable by the person so as to shift or pull his lower jaw forwardly of its normal position.

In one form thereof, the present inventions is directed to an anti-snoring device including upper and lower trays having a generally rigid outer shell and an inner moldable portion. The trays are adapted to fit over a person's upper and lower teeth with the teeth at least partially pressed into the moldable portion. The upper and lower trays are selectively detachably attachable to one another. Each of the trays are generally arcuate shaped with a central portion adapted to fit over a person's front teeth and a posterior portion on each side of the central portion. At least one of the rigid outer shells include a depression whereby when the trays are placed on a person's upper and lower teeth, a breathing opening is provided between the trays rigid outer shells.

In one form thereof, the present invention is directed to an anti-snoring device including upper and lower trays having a generally rigid outer shell and an inner moldable portion. The trays are adapted to fit over a person's upper and lower teeth with the teeth at least partially pressed into the moldable portion. The upper and lower trays are selectively detachably attachable to one another. Each of the trays are generally arcuate shaped with a central portion adapted to fit over a person's front teeth and a posterior portion on each side of the central portions. The trays rigid outer shells include depressions in the posterior portions on each side of the central portion whereby when the trays are placed on a person's upper and lower teeth, the upper tray depressions are aligned with the lower tray depressions for thereby providing breathing openings on each side of the central portions and between the trays.

BRIEF DESCRIPTION OF THE DRAWINGS

The above-mentioned and other features and objects of this invention and the manner of obtaining them will become more apparent and the invention itself will be better understood by reference to the following description of embodiments of the invention taken in conjunction with the accompanying drawings wherein:

FIG. 1 is a perspective view of the upper and lower trays constructed in accordance with the principles of the present invention and detached from one another;

FIG. 2 is a side elevation view of the upper and lower trays shown in FIG. 1 and shown attached to one another;

FIG. 3 is a front elevation view of the trays shown in FIG. 1 and attached to one another;

FIG. 4 is a vertical cross-sectional view of the trays taken generally along line 4—4 in FIG. 2;

FIG. 5 is a vertical cross-sectional view of the trays taken generally along line 5—5 in FIG. 2;

FIG. 6 is a vertical cross-sectional view of the trays taken generally along line 6—6 in FIG. 3; and, FIG. 7 is a perspective view of one of the trays showing the terminal ends of the posterior portions.

Corresponding characters indicate corresponding parts throughout the several views of the drawings.

The exemplifications set out herein illustrate preferred embodiments of the invention in one form thereof and such exemplifications are not to be construed as limiting the scope of the disclosure or the scope of the invention in any manner.

DETAILED DESCRIPTION OF SPECIFIC EMBODIMENTS

As shown in the drawings, the anti-snoring device generally depicted by the numeral 10 includes an upper tray 12 and a lower tray 14. The upper tray 12 is adapted to fit over a person's upper teeth 16 and the lower tray 14 is adapted to fit over a person's lower teeth 18. Although, reference is made herein to "upper" and "lower" trays, as shown in the drawings and as more fully discussed hereinbelow, it is noted that the upper and lower trays 12 and 14 are in fact interchangeable and, thus, as used herein, the terms "upper" and "lower" are used merely for referencing the component parts of the anti-snoring device.

Both the upper and lower trays 12 and 14 are generally arcuate shaped as shown having a central or front portion 20 and posterior portions 22 on each side of the central portions 20. The posterior portions 22 have terminal ends 24 which terminate just prior to the person's molars or at about the premolars as shown.

As best seen in FIGS. 4–6, upper and lower trays 12 and 14 are generally U-shaped in cross section having an outer rigid shell 26 and an inner moldable portion 28. The outer rigid shell 26 is preferably made of a hard or rigid plastic and is formed by injection molding. The inner moldable portion 28 is preferably made of the thermoplastic material which can be selectively molded by heating to temperatures greater than about 115° F. In the preferred embodiment, after the outer rigid shell 26 is injection molded and formed, the U-shaped cavity is filled with the thermoplastic moldable portion 28. For fitting over a person's teeth, the upper and lower trays 12 and 14 are heated such as by placing in hot water having a temperature greater about 115° F. Thereafter, the trays are placed into the person's mouth and the person bites into the inner moldable portions 28 causing their teeth to sink into the moldable portions 28 and causing the thermoplastic material thereof to be formed and set around the person's teeth. In this fashion, the upper tray 12 is fitted generally perfectly over a person's upper teeth 16 and the lower tray 14 is fitted generally perfectly over the person's lower teeth 18.

So as to detachably attach the upper and lower trays 12 and 14 to one another and selectively shift the lower tray 14 and the person's jaw forward of its normal position, the upper tray 12 is provided with a tongue 30 and the lower tray 14 is provided with a tongue 32. As best seen in FIG. 6, tongues 30 and 32 are integrally formed with the rigid plastic outer shells 26 of respective upper and lower trays 12 and 14. Tongues 30 and 32 are located at and extend forwardly from the central portions 20. Tongues 30 and 32 are generally flat and thin as shown in planes generally parallel with one another when the upper and lower trays 12 and 14 are placed adjacent to one another as best seen in FIGS. 2, 3 and 6. In this manner, when the upper and lower trays 12 and 14 are placed in a person's mouth, the tongues 30 and 32 easily and comfortably extend out of the person's mouth and between the person's lips.

The upper tray tongue 30 is provided with a plurality of holes 34 which are aligned as shown in a line generally directly forwardly of the central portion 20. The lower tray tongue 32 is provided with a projection or protrusion 36 which, as best seen in FIG. 6, is adapted to selectively snap fit into any one of the holes 34. Thus, tongues 30 and 32 and their respective upper and lower trays 12 and 14 are selectively detachably attachable to one another by selectively pressing the projection 36 into any one of the holes 34 or removing the projection 36 by merely pulling the tongue and forcing the projection 36 out from frictional engagement within a hole 34.

In use, after the upper and lower trays 12 and 14 have been molded and fitted over the person's teeth, the lower tray is attached to the upper tray slightly forwardly from the normal position. Thus, when the upper and lower trays are placed over the person's teeth, the lower tray 14 as well as the person's lower teeth 18 and jaw are forced slightly forwardly with respect to the upper tray 12 and upper teeth 16. In this manner, the person's tongue is also forced slightly forwardly thereby helping to retain the air passageway open and unobstructed. Typically, the lower jaw need only be shifted about 3–6 millimeters forward from its normal position and, therefore, holes 34 are preferably located 2–3 millimeters from each other thereby allowing the person to shift the lower jaw as may be desired and as can be tolerated.

Since most people who snore typically prefer breathing through their mouths, the upper and lower trays 12 and 14 are further provided with depressions 38 formed in the rigid outer shells 26. Depressions 38 are preferably located in the posterior portions 22 on each side of the central portions. Essentially, the rigid shells 26 at the bottom of the U-shaped section are relieved or depressed toward the moldable portions 28 so as to thereby form the depressions 38 as shown and best seen in FIGS. 1 and 4. The depressions 38 in the upper and lower trays 12 and 14 are aligned such that, when the trays are placed adjacent to one another and on a person's upper and lower teeth, the depressions 38 of upper tray 12 align with the depressions 38 of lower tray 14 thereby forming breathing openings 40 on each side of the central portions and between the trays as best shown in FIGS. 2 and 3. Most preferably, the depressions 38 and, thus, breathing openings 40, are placed in the posterior portions 22 but generally close to the central portions 20.

While the invention has been described as having specific embodiments, it will be understood that it is capable of further modifications. This application, is therefore, intended to cover any variations, uses, or adaptations of the invention following the general principles thereof and including such departures from the present disclosure as come within known or customary practice in the art to which this invention pertains and fall within the limits of the appended claims.

What is claimed is:

1. An anti-snoring device comprising:
   upper and lower trays having a generally rigid outer shell and an inner moldable portion, said trays adapted to fit over a person's upper and lower teeth with the teeth at least partially pressed into said moldable portion;
   wherein said upper and lower trays are selectively detachably attachable to one another;
   each of said trays being generally arcuate shaped with a central portion adapted to fit over a person's front teeth and a posterior portion on each side of said central portion;
   wherein at least one tray rigid outer shell includes a depression whereby, when said trays are placed on a person's upper and lower teeth, a breathing opening is provided between said trays rigid outer shells; and
   wherein said depression is located in a posterior portion of a tray.

2. The anti-snoring device of claim 1 wherein said rigid outer shell depression extends into said inner moldable portion.

3. The anti-snoring device of claim 2 further comprising a tongue extending from each of said central portions of said upper and lower trays rigid outer shells, said tongues including means for detachably attaching said tongues to one another.

4. The anti-snoring device of claim 3 wherein said tongues are integrally formed with said respective tray rigid outer shell.

5. The anti-snoring device of claim 4 wherein said moldable portions are thermoplastic and are adapted to be selectively moldable at temperatures greater than about 115° F.

6. The anti-snoring device of claim 5 wherein said posterior portions extend a distance on each side of said central portions such that said posterior portions terminate at about the person's premolars.

7. The anti-snoring device of claim 2 further comprising a tongue extending from said central portion of each of said upper and lower trays rigid outer shells, one of said tongues including a plurality of holes, the other of said tongues including a projection adapted to selectively snap fit into any one of said other tongue holes, whereby said trays are selectively detachably attachable to one another in a plurality of positions.

8. The anti-snoring device of claim 7 wherein said tongues are integrally formed with said respective tray rigid outer shell.

9. The anti-snoring device of claim 7 wherein said moldable portions are thermoplastic and are adapted to be selectively moldable at temperatures greater than about 115° F.

10. The anti-snoring device of claim 9 wherein said posterior portions extend a distance on each side of said central portions such that said posterior portions terminate at about the person's premolars.

11. The anti-snoring device of claim 1 further comprising a tongue extending from each of said central portions of said upper and lower trays rigid outer shells, said tongues including means for detachably attaching said tongues to one another.

12. The anti-snoring device of claim 11 wherein said tongues are integrally formed with said respective tray rigid outer shell.

13. The anti-snoring device of claim 1 further comprising a tongue extending from said central portion of each of said upper and lower trays rigid outer shells, one of said tongues including a plurality of holes, the other of said tongues including a projection adapted to selectively snap fit into any one of said other tongue holes, whereby said trays are selectively detachably attachable to one another in a plurality of positions.

14. The anti-snoring device of claim 13 wherein said tongues are integrally formed with said respective tray rigid outer shell.

15. An anti-snoring device comprising:
   upper and lower trays having a generally rigid outer shell and an inner moldable portion, said trays adapted to fit over a person's upper and lower teeth with the teeth at least partially pressed into said moldable portion;
   wherein said upper and lower trays are selectively detachably attachable to one another;
   each of said trays being generally arcuate shaped with a central portion adapted to fit over a person's front teeth and a posterior portion on each side of said central portion;
   wherein at least one tray rigid outer shell includes a depression whereby, when said trays are placed on a person's upper and lower teeth, a breathing opening is provided between said trays rigid outer shells; and,
   wherein said moldable portions are thermoplastic and are adapted to be selectively moldable at temperatures greater than about 115° F.

16. An anti-snoring device comprising:
   upper and lower trays having a generally rigid outer shell and an inner moldable portion, said trays adapted to fit over a person's upper and lower teeth with the teeth at least partially pressed into said moldable portion;
   wherein said upper and lower trays are selectively detachably attachable to one another;
   each of said trays being generally arcuate shaped with a central portion adapted to fit over a person's front teeth and a posterior portion on each side of said central portion;
   wherein at least one tray rigid outer shell includes a depression whereby, when said trays are placed on a person's upper and lower teeth, a breathing opening is provided between said trays rigid outer shells; and,
   wherein said posterior portions extend a distance on each side of said central portions such that said posterior portions terminate at about the person's premolars.

17. An anti-snoring device comprising:
   upper and lower trays having a generally rigid outer shell and an inner moldable portion, said trays adapted to fit over a person's upper and lower teeth with the teeth at least partially pressed into said moldable portion;
   wherein said upper and lower trays are selectively detachably attachable to one another;
   each of said trays being generally arcuate shaped with a central portion adapted to fit over a person's front teeth and a posterior portion on each side of said central portion;

wherein at least one tray rigid outer shell includes a depression whereby, when said trays are placed on a person's upper and lower teeth, a breathing opening is provided between said trays rigid outer shells; and, wherein said rigid outer shell depression extends into said inner moldable portion.

18. An anti-snoring device comprising:

upper and lower trays having a generally rigid outer shell and an inner moldable portion, said trays adapted to fit over a person's upper and lower teeth with the teeth at least partially pressed into said moldable portion;

wherein said upper and lower trays are selectively detachably attachable to one another;

each of said trays being generally arcuate shaped with a central portion adapted to fit over a person's front teeth and a posterior portion on each side of said central portion;

wherein said trays rigid outer shells include depressions in said posterior portions on each side of said central portion whereby, when said trays are placed on a person's upper and lower teeth, said upper tray depressions are aligned with said lower tray depressions for thereby providing breathing openings on each side of said central portions and between said trays; and, wherein said moldable portions are thermoplastic and are adapted to be selectively moldable at temperatures greater than about 115° F.

19. The anti-snoring device of claim 18 further comprising a tongue extending from each of said central portions of said upper and lower trays rigid outer shells, said tongues including means for detachably attaching said tongues to one another.

20. The anti-snoring device of claim 19 wherein said tongues are integrally formed with said respective tray rigid outer shell.

21. The anti-snoring device of claim 18 further comprising a tongue extending from said central portion of each of said upper and lower trays rigid outer shells, one of said tongues including a plurality of holes, the other of said tongues including a projection adapted to selectively snap fit into any one of said other tongue holes, whereby said trays are selectively detachably attachable to one another in a plurality of positions.

22. The anti-snoring device of claim 21 wherein said tongues are integrally formed with said respective tray rigid outer shell.

23. The anti-snoring device of claim 22 wherein said moldable portions are thermoplastic and are adapted to be selectively moldable at temperatures greater than about 115° F.

24. The anti-snoring device of claim 18 wherein said moldable portions are thermoplastic and are adapted to be selectively moldable at temperatures greater than about 115° F.

25. The anti-snoring device of claim 18 wherein said posterior portions extend a distance on each side of said central portions such that said posterior portions terminate at about the person's premolars.

26. An anti-snoring device comprising:

upper and lower trays having a generally rigid outer shell and an inner moldable portion, said trays adapted to fit over a person's upper and lower teeth with the teeth at least partially pressed into said moldable portion;

wherein said upper and lower trays are selectively detachably attachable to one another;

each of said trays being generally arcuate shaped with a central portion adapted to fit over a person's front teeth and a posterior portion on each side of said central portion;

wherein said trays rigid outer shells include depressions in said posterior portions on each side of said central portion whereby, when said trays are placed on a person's upper and lower teeth, said upper tray depressions are aligned with said lower tray depressions for thereby providing breathing openings on each side of said central portions and between said trays; and, wherein said rigid outer shell depressions extend into said inner moldable portions.

27. The anti-snoring device of claim 26 wherein said moldable portions are thermoplastic and are adapted to be selectively moldable at temperatures greater than about 115° F.

28. The anti-snoring device of claim 27 wherein said posterior portions extend a distance on each side of said central portions such that said posterior portions terminate at about the person's premolars.

29. The anti-snoring device of claim 26 wherein said posterior portions extend a distance on each side of said central portions such that said posterior portions terminate at about the person's premolars.

* * * * *